United States Patent [19]

Phillips

[11] 4,164,406
[45] Aug. 14, 1979

[54] PHOSPHINYLPHTHALIMIDINES AND THEIR USE AS PLANT GROWTH REGULANTS

[75] Inventor: Wendel G. Phillips, Manchester, Mo.

[73] Assignee: Monsanto Company, St. Louis, Mo.

[21] Appl. No.: 596,027

[22] Filed: Jul. 11, 1975

[51] Int. Cl.² .................... A01N 9/36; A01N 9/00; C07D 209/34
[52] U.S. Cl. ........................... 71/86; 71/76; 71/71; 260/325 PH
[58] Field of Search ............... 260/325 PH; 71/96, 86, 71/76

[56] References Cited
U.S. PATENT DOCUMENTS

| | | | |
|---|---|---|---|
| 2,973,369 | 2/1961 | Pugin | 260/325 PH |
| 3,317,558 | 5/1967 | Becke et al. | 260/325 PH |

*Primary Examiner*—Glennon H. Hollrah
*Attorney, Agent, or Firm*—Richard H. Shear; Donald W. Peterson

[57] ABSTRACT

Effective plant growth regulation is obtained by application to the plant of compounds having the formula

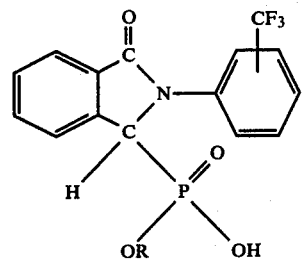

wherein R is hydrogen or lower alkyl.

15 Claims, No Drawings

PHOSPHINYLPHTHALIMIDINES AND THEIR USE AS PLANT GROWTH REGULANTS

This invention relates to a novel class of chemical compounds and their use as plant growth regulators. More particularly, this invention relates to phthalimidine compounds having the formula

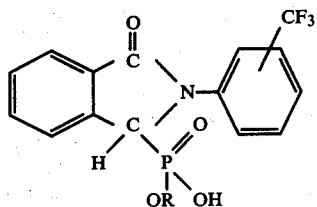
(I)

wherein R is either hydrogen or lower alkyl. By the term "lower alkyl" as used herein is meant those alkyl groups having from 1 to 4 carbon atoms.

Preferred compounds are those of the above formula in which the $CF_3$ moiety is in the meta position. Most preferred are those compounds in which R is hydrogen or ethyl. For purposes of clarity, the most preferred compounds are identified by the formulae below.

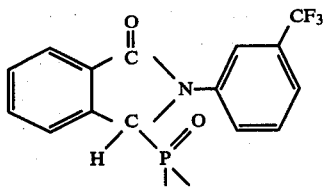
(A)

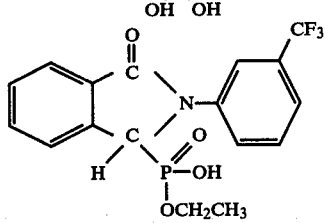
(B)

As mentioned above, the compounds of the invention are effective as plant growth regulants. The term "plant regulant," or "plant growth regulant", as employed in this application, connotes a material which serves to modify the normal sequential development of a treated plant to agricultural maturity. Such modification may result from the effect of the material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alteration, increased branching, tillering, terminal inhibition, increased flowering or fruit set, increased root growth, stool or sprout inhibition, delayed budding, defoliation, desiccation, delayed senescence, prolongated dormancy, increased cold hardiness, delayed or accelerated ripening, thinning of fruit, prevention of pre-harvest fruit drop, loosening of fruit and the like.

Modifications in the normal sequential development of a treated plant to agricultural maturity may also be manifested by reduced transpiration or increased carbohydrate deposition or protein content.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Further, a reduction in the maturation rate on portions of a crop permits an extended harvest period at peak yield and more efficient use of subsequent crop processing equipment.

It is to be understood that the regulation of plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention, desirable modification of plants may be achieved by applying the above-described plant regulants to seeds, emerging seedlings, roots, stems, leaves, flowers, fruits or other plant parts. Such application may be made directly to the plant part, or indirectly by application to the plant growing medium.

The term "active ingredient" will be used hereinafter in this specification to describe the active phthalimidines of the foregoing formula. In practicing the plant growth regulating methods of this invention, the active ingredients can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

Illustrative finely divided solid carriers and extenders which are useful in the plant growth regulating compositions of this invention, include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents include, for example, Stoddard solvent, acetone, alcohols, glycols, ethyl acetate, benzene and the like. The plant growth regulating compositions of this invention, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. The application of the plant growth regulating compositions to the plant growth medium is generally carried out by incorporating the compositions in the soil or other media in the area where modification of the plants is desired.

In selecting the appropriate non-toxic rate of application of the active ingredient it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts from about 0.05 to about 10 or more pounds per acre (0.056 to 11.2 kilos per hectare). Foliar applications of from 1 to 5 pounds of the active ingredient per acre (1.12 to 5.6 kilos per hectare) are preferred. In applications to the soil habitat of germinant seeds, emerging seedlings, and established vegetation for the regulation of plant growth, the active ingredients are applied in amounts of from about 0.01 to about 20 pounds per acre (0.011 to 22.4 kilos per hectare) or more. Preferably, the active ingredients are applied to the soil at a rate of from 1 to 10 pounds per acre (1.12 to 11.2 kilos per hectare). Foliar application to plants beginning to blossom are particularly advantageous and are preferred.

In accordance with this invention it has been found that the phthalimidines of the foregoing formula are highly effective plant growth regulants. This particular class of chemical compounds, when applied to dicotyledonous plants, are effective for reducing the stature of the plant with appreciable improvement in the plant's vigor. Thus, one embodiment of the present invention is a method which comprises applying to viable dicotyledonous plants a growth regulating amount of one or more of the phthalimidines of the foregoing formula. Of particular importance is the application of the phthalimidines of the invention to leguminous plants, such as soybeans. The practice of this invention provides means for obtaining plants of reduced stature whereby the growing energy utilized by the plant is channeled more toward fruiting and less toward vegetative growth. Many plants of reduced stature obtained by the present method are more tolerant of drought and cold temperatures and are more resistant to pest infestations and lodging. The method also provides for plants that are in a good state of health and tends to produce more vigorous and prolific plants. The method of the present invention can be conveniently carried out to obtain plants of reduced stature without substantial injury to the plants.

The practice of the method of this invention can be utilized for improving the efficiency of dicotyledonous crop plants such as soybean (Glycine), cotton (Gossypium), beans (Phaseolus), coffee (Coffea) and the like which often do not obtain their yield capacity due to premature blossom drop or because of failure of the fruit to set. The application of the phthalimidines to such growing crop plants reduces the plant stature and improves the fruit set. In this manner, the plant's efficiency of production is improved and a means is provided for optimizing the crop by increasing the plant population per unit area. Also, such reduction in plant stature increases accessibility to the field for other treatments, cultivation and harvesting.

In accordance with the practice of the present invention, plant growth regulating compositions were formulated using compounds (A) and (B) of the above formulae as the active ingredient. The compositions were formulated so that they could be applied in tests at a rate the equivalent of 200 gallons per acre (302 liters per hectare). Table I illustrates the formulation of the composition for several application rates of active ingredient. In each formulation, the stock solution utilized is 1% of the active ingredient dissolved in acetone.

TABLE I

| RATE Lbs/Acre (kilos/hectare) | ml. of 1% Stock Solution | ml. Acetone | ml. 0.39% TWEEN 20 In Water As Surfactant |
|---|---|---|---|
| 6.0 (6.72) | 2.0 | — | 3.6 |
| 5.0 (5.60) | 2.0 | 1.0 | 3.7 |
| 3.0 (3.36) | 1.0 | 1.0 | 3.6 |
| 2.5 (2.80) | 1.0 | 2.0 | 3.7 |
| 1.2 (1.34) | 0.4 | 1.6 | 3.6 |
| 1.0 (1.12) | 0.4 | 2.6 | 3.7 |
| 0.6 (.672) | 0.2 | 1.8 | 3.6 |
| 0.5 (.560) | 0.2 | 2.8 | 3.7 |
| 0.3 (.336) | 0.1 | 1.9 | 3.6 |

Utilizing compositions formulated in accordance with Table I, the phthalimidines exhibited plant growth regulatory properties as illustrated by the test set forth in Example 1.

EXAMPLE 1

A number of soybean plants, variety Corsoy, are grown from seeds in aluminum pans in the greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with Table I is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and two weeks after application represents the increase in the development of the treated pans. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction, or an increase in growth in excess of 25% of that of the control plants, i.e., growth stimulation.

Table II below summarizes the results and observations made in accordance with Example 1 when compounds (A) and (B) of the invention were utilized as the active ingredient at several rates.

TABLE II

| Compound | Rate lb/acre (kilos/hectare) | Results |
|---|---|---|
| A | 6.0 (6.72) | Stature reduction, axillary bud development, stem distortion, rosette growth, slight leaf burn |
|  | 3.0 (3.36) | Stature reduction, axillary bud development, rosette growth, slight leaf burn |
|  | 1.2 (1.34) | Stature reduction, axillary bud development, chlorosis, rosette growth |
|  | 0.6 (0.672) | Stature reduction, axillary bud development, altered canopy |
|  | 0.3 (0.336) | Stature reduction, axillary bud development, altered canopy |
| B | 6.0 (6.72) | Stature reduction, chlorosis, axillary bud development, rosette growth |
|  | 3.0 (3.36) | Stature reduction, chlorosis, axillary bud development, stem distortion, rosette growth |
|  | 1.2 (1.34) | Stature reduction, chlorosis, axillary bud development, stem distortion, altered canopy |
|  | 0.6 (0.672) | Axillary bud development, stem distortion, altered canopy |

Further aspects of this invention are shown in the following examples.

EXAMPLE 2

Individual soybean plants, variety Corsoy, are grown from seed in 6 inch (15.24 cm) pots containing a good grade of top soil. Two pots of 6-week old plants (5-6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations made utilizing the test procedure of Example 2 are summarized in Table III.

TABLE III

| Compound | Rate lb/acre (kilos/hectare) | Results |
|---|---|---|
| A | 1.0 (1.12) | Leaf distortion |
|  | 0.5 (0.56) | Leaf distortion |
|  | 0.25 (0.28) | No response |
| B | 2.5 (2.8) | Stature reduction, leaf distortion |
| B | 1.0 (1.12) | No response |
|  | 0.5 (0.56) | No response |

In accordance with the above results, it is preferred that higher rates of application (one pound per acre—1.12 kilos/hectare—and above) be utilized in regulating the growth of plants.

EXAMPLE 3

The procedure of Example 1 was repeated by applying the plant growth regulating compositions to cotton plants when the plants were 2 to 3 weeks old. Results obtained are noted in Table IV.

TABLE IV

| Compound | Rate lb/acre (kilos/hectare) | Results |
|---|---|---|
| A | 3.0 (3.36) | Altered canopy |
|  | 1.2 (1.34) | Altered canopy |
|  | 0.6 (0.672) | Leaf distortion |
|  | 0.3 (0.336) | Stature reduction, altered canopy |
| B | 3.0 (3.36) | Axillary bud development, altered canopy |
|  | 1.2 (1.34) | Stature reduction, axillary bud development, altered canopy |
|  | 0.6 (0.672) | No response |

EXAMPLE 4

The procedure of Example 1 was again repeated by applying the plant growth regulating compositions to tomato plants when the plants were 2 to 3 weeks old. Results obtained are noted in Table V.

TABLE V

| Compound | Rate lb/acre (kilos/hectare) | Results |
|---|---|---|
| A | 3.0 (3.36) | Axillary bud development, leaf distortion, leaf alteration, altered canopy |
|  | 1.2 (1.34) | Axillary bud development, leaf distortion, altered canopy |
|  | 0.6 (0.672) | Leaf distortion, altered canopy |
|  | 0.3 (0.336) | Leaf distortion |
| B | 3.0 | Leaf distortion, altered |

TABLE V-continued

| Compound | Rate lb/acre (kilos/hectare) | Results |
|---|---|---|
| | (3.36) | canopy |
| | 1.2 | Stature reduction |
| | (1.34) | |
| | 0.6 | No response |
| | (0.672) | |

Generally, the compounds of the invention may be prepared by the following reaction scheme:

1.
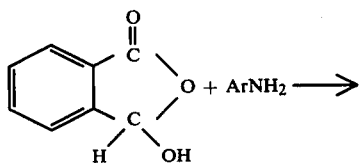

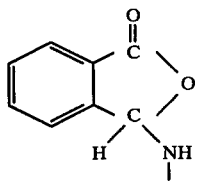

2.
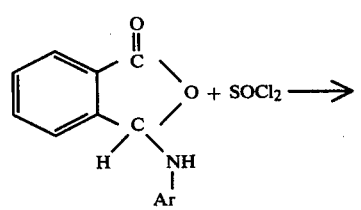

3.
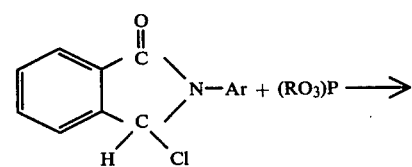

4.
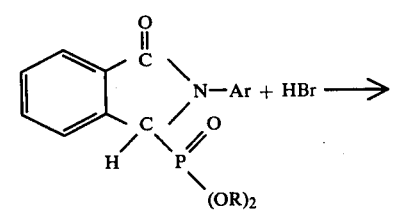

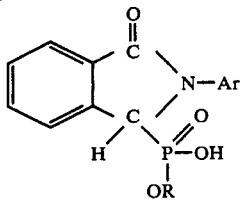

In step 1 of the reaction scheme phthaldehydic acid is reacted with a stoichiometric amount of an appropriate aniline in an inert solvent and heated between room temperature and the reflux temperature of the system. An excess amount of thionyl chloride is then added to the solid product of step 1 to obtain a chlorophthalimidine (step 2). To the chlorophthalimidine is added an equivalent or excess amount of an appropriate phosphite to obtain a 3-phosphonophthalimidine (step 3). Finally, in step 4, a hydrobromic acid hydrolysis of 3-phosphonophthalimidine yields the compounds of the invention.

Whether the final product obtained is an acid such as compound (A) or a half ester such as compound (B) is dependent upon the conditions of the hydrobromic acid hydrolysis (step 4). Harsh conditions, i.e., heat at reflux, are utilized to obtain acids such as compound (A). Less harsh conditions, i.e., heat at temperatures below the reflux temperature of the system, are utilized to obtain half esters such as compound (B).

In order to more fully illustrate the manner of preparation of the compounds of the invention, the following examples are presented.

EXAMPLE 5

Preparation of 2(m-trifluoromethylphenyl)-3-(di-ethoxyphosphinyl)phthalimidine

Triethylphosphite (8.3 g, 0.05 M) was added to 15.6 g (0.05 M) of 2-(m,alpha,alpha,alpha-trifluorotolyl)-3-chlorophthalimidine and the mixture melted together on the steam bath. The mixture resolidified and was allowed to cool. Petroleum ether (b.p. 30–75 degrees, 200 ml) was added, the mixture stirred well and filtered to give 16.3 g (79%). The product was recrystallized from ethanol/water to give 14.1 g, m.p. 119–121 degrees.

Anal. calcd. for $C_{19}H_{19}F_3NO_4P$: C, 55.21; H, 4.63; N, 3.39. Found: C, 55.33; H, 4.94; N, 3.29.

EXAMPLE 6

Preparation of 2-(m-trifluoromethylphenyl)-3-(dimethoxyphosphinyl)phthalimidine

This compound was prepared as above using 15.6 g (0.05 M) of 2-(m,alpha,alpha,alpha-trifluorotolyl)-3-chlorophthalimidine and 5.1 g (0.05 M) of trimethylphosphite to give 14.3 g crude product. This material was recrystallized from methylene chloride/petroleum ether (b.p. 30–75 degrees) to give 1.9 g of crude 2-(m,alpha,alpha,alpha-trifluorotolyl) 3-hydroxy phthalimidine. The filtrate was concentrated to give 8.9 g of product, m.p. 123–125 degrees. Recrystallization of this product from methylene chloride/petroleum ether (b.p. 30–75 degrees) gave 3.6 g, m.p. 125–126 degrees.

Anal. calc. for $C_{17}H_{15}F_3NO_4P$: C, 53.00; H, 3.92; N, 3.64. Found: C, 53.30; H, 4.05; N, 3.39.

EXAMPLE 7

Preparation of N-(m-trifluoromethylphenyl)-3-Ethoxy-3-Hydroxy-phosphinylphthalimidine A mixture of 7.8 g (0.025 mol) of 2(m-alpha,alpha,alpha-trifluorotolyl)-3-diethoxy-phosphinylphthalimidine and 50 ml conc. hydrobromic acid was heated 15 minutes on a steam bath and cooled. The hydrobromic acid was decanted and the oily residue washed with water. This material was treated with 5% NaOH solution. The insoluble portion was collected and shown to be starting material by NMR and its mp. 100-107 degrees.

The filtrate was acidified and 1.0 g of a solid was collected, mp 176-179 degrees.

Anal. Calc. for $C_{17}H_{15}F_3NO_4P$: C, 52.99; H, 3.92; N, 3.64. Found: C, 52.83; H, 3.92; N, 3.57.

EXAMPLE 8

Preparation of N-(m-trifluoromethylphenyl)-3,3-dihydroxyphosphinylphthalimidine

A mixture of 7.8 g (0.025 mol) of 2(m-alpha,alpha,alpha-trifluorotolyl)-3-diethoxy-phosphinylphthalimidine and 50 ml of concentrated hydrobromic acid were mixed together and heated at reflux for three hours. Overnight 5.0 g of a crystalline solid was obtained. Recrystallization with ethyl acetate yielded another 2.5 g portion.

Anal. Calc. C, 50.43; H, 3.10; N, 3.92. Found C, 50.48; H, 3.91; N, 3.54.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

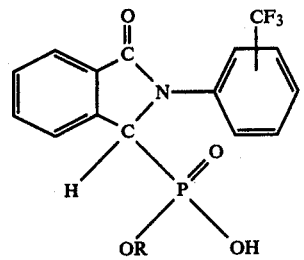

wherein R is hydrogen or lower alkyl.

2. A compound according to claim 1 wherein said $CF_3$ moiety is in the meta position.
3. A compound according to claim 1 wherein R is hydrogen.
4. A compound according to claim 1 wherein R is ethyl.
5. A compound according to claim 2 wherein R is hydrogen.
6. A compound according to claim 2 wherein R is ethyl.
7. A method of regulating the growth of dicotyledanous plants which comprises treating said plant with an effective non-lethol amount of a compound having the formula

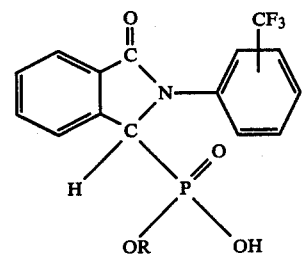

wherein R is hydrogen or lower alkyl.

8. A method according to claim 7 wherein said $CF_3$ moiety is in the meta position.
9. A method according to claim 7 wherein R is hydrogen.
10. A method according to claim 7 wherein R is ethyl.
11. A method according to claim 7 wherein said plants are treated with said compound at a rate above about 1.0 pound per acre.
12. A method according to claim 8 wherein R is hydrogen.
13. A method according to claim 8 wherein R is ethyl.
14. A method according to claim 7 wherein said plants are legumes.
15. A method according to claim 14 wherein said plants are soybeans.

* * * * *